United States Patent
Mills et al.

(10) Patent No.: US 11,886,043 B2
(45) Date of Patent: Jan. 30, 2024

(54) WEARABLE OPTICAL DEVICES

(71) Applicant: BAE SYSTEMS plc, London (GB)

(72) Inventors: Rory Thomas Alexander Mills, Rochester (GB); Ian Thomas Macken, Rochester (GB)

(73) Assignee: BAE SYSTEMS plc, London (GB)

( * ) Notice: Subject to any disclaimer, the term of this patent is extended or adjusted under 35 U.S.C. 154(b) by 658 days.

(21) Appl. No.: 17/055,393

(22) PCT Filed: Apr. 30, 2019

(86) PCT No.: PCT/GB2019/051192
§ 371 (c)(1),
(2) Date: Nov. 13, 2020

(87) PCT Pub. No.: WO2019/220075
PCT Pub. Date: Nov. 21, 2019

(65) Prior Publication Data
US 2021/0208421 A1 Jul. 8, 2021

(30) Foreign Application Priority Data

May 18, 2018 (EP) .................................... 18173242
May 18, 2018 (GB) .................................... 1808076

(51) Int. Cl.
*G02C 5/02* (2006.01)
*G02B 27/01* (2006.01)
*A61F 9/02* (2006.01)

(52) U.S. Cl.
CPC ........... *G02C 5/02* (2013.01); *G02B 27/0176* (2013.01); *G02B 27/0179* (2013.01);
(Continued)

(58) Field of Classification Search
USPC ......................................................... 351/124
See application file for complete search history.

(56) References Cited

U.S. PATENT DOCUMENTS

| 4,762,406 A | 8/1988 | Steiner |
| 2013/0079850 A1* | 3/2013 | Darvish ................. A61B 18/22 |
| | | 607/90 |

(Continued)

FOREIGN PATENT DOCUMENTS

| CN | 203815063 U | 9/2014 |
| EP | 3081981 A1 | 10/2016 |

(Continued)

OTHER PUBLICATIONS

International Preliminary Report on Patentability received for PCT Application No. PCT/GB2019/051192 dated Dec. 3, 2020. 8 pages.

(Continued)

*Primary Examiner* — Darryl J Collins
(74) *Attorney, Agent, or Firm* — Finch & Maloney PLLC

(57) ABSTRACT

A modular wearable optics device including: at least one wearable support element; one or more active optical elements adapted in use to display an image to a user; one of a plurality of bridging elements selected to position or orientate the one or more active optical elements in a predetermined location based on one or more anthropometric characteristics of the user.

18 Claims, 4 Drawing Sheets

(52) U.S. Cl.
CPC ...... *A61F 9/029* (2013.01); *G02B 2027/0178* (2013.01); *G02B 2027/0181* (2013.01); *G02C 2200/08* (2013.01)

(56) References Cited

U.S. PATENT DOCUMENTS

| | | |
|---|---|---|
| 2013/0250503 A1 | 9/2013 | Olsson et al. |
| 2013/0318776 A1 | 12/2013 | Jacobs et al. |
| 2015/0103306 A1* | 4/2015 | Kaji .................. G02B 27/0179 351/128 |
| 2017/0108713 A1* | 4/2017 | Blum .................. H01R 33/945 |
| 2018/0129068 A1* | 5/2018 | Allione .................. G02C 5/045 |

FOREIGN PATENT DOCUMENTS

| | | | |
|---|---|---|---|
| GB | 2410805 A | 10/2005 | |
| WO | 2016119435 A1 | 8/2016 | |
| WO | 2017093955 A1 | 6/2017 | |
| WO | 2019220075 A1 | 11/2019 | |

OTHER PUBLICATIONS

International Search Report and Written Opinion received for PCT Application No. PCT/GB2019/051192 dated Jul. 19, 2019. 13 pages.
GB Search Report under Section 17(5) received for GB Application No. 1808076.2 dated Oct. 10, 2018. 3 pages.
Extended European Search Report received for EP Application No. 18173242.1, dated Nov. 30, 2018. 7 pages.

* cited by examiner

WEARABLE OPTICAL DEVICES

The present invention relates to improvements in or relating to wearable optical devices, particularly but not exclusively to adjustable wearable devices.

Wearable optical devices are common in many walks of life. These include automotive applications, aviation, military applications, engineering, medicine, gaming and any general application for viewing media and the like. Wearable optical devices are often referred to as head mounted displays (HMD) or head worn displays (HWD); the expression 'HMD' is used herein to represent HMDs, HWDs and any other wearable optical devices such as, for example, goggles, glasses and hand held devices with viewing capabilities. Most HMD include two eye pieces, one for each eye.

HMDs are used for many applications as indicated above, however there is a continual problem encountered in their use. This is that they tend suffer from alignment problems with respect to aligning the viewable output to the human eye. This makes viewing less comfortable or more difficult than would be desired. When designing an HMD, anthropometric data (relating to skull dimensions and body proportions) are taken into consideration. This helps with the viewing comfort but only to a limited extent. One main problem is that users each have a different interpupillary distance (IPD). As a result the ideal positions of the eyepieces from one user to the next would be different. Achieving a stable means of adjusting the IPD for individual users has proved difficult.

Accordingly, one object of the present invention is to overcome the problems of existing HMDs.

A further object is to provide a HMD or the like in which the alignment problems are at least ameliorated, if not overcome.

SUMMARY

According to an aspect of the present invention there is provided a modular wearable optics device including: at least one wearable support element; one or more active optical elements adapted in use to display an image to a user; one of a plurality of bridging elements selected to position or orientate the one or more active optical elements in a predetermined location based on one or more anthropometric characteristics of the user.

Preferably, an optical system is included which is enabled to adjust one or more convergence parameters of the eyepieces.

Preferably, further comprising a plurality of bridging elements having different shapes and sizes each adapted to locate the eyepieces in a different position or orientation.

Preferably, bridging element includes an identifier which enables identification of the shape and size of the bridging element to thereby adjust one or more convergence parameters of the eyepiece.

Preferably, the one or more convergence parameters are adjustable by the optical system.

Preferably, the eyepieces are adapted to be angularly displaceable to create a wider field of view for the display Preferably, the anthropometric characteristics based on the interpupillary distance of the user.

Preferably, the bridging element is selected based on the interpupillary distance of the user.

Preferably, the optical element include at least one of an active optical element and an inactive optical element.

Preferably, the or each optical element includes a predetermined active optical area.

Preferably, the active area is surrounded by an inactive area.

Preferably, the wearable support element comprises at least one of a frames; side arms and supports for goggles or glasses; a helmet or visor; a headband; a neck or shoulder worn support; and a headset.

Preferably, each bridging element is a band having a combination of a different curvature and a different length.

Preferably, the bridging element is a shaped element adapted to support the eyepieces in a predetermined position or orientation.

According to a further aspect of the present invention there is provided one or more eyepieces for use with the modular wearable optics device of another aspect of the invention.

According to a further aspect of the present invention there is provided one or more bridging elements for use with the modular wearable optics device of another aspect of the invention.

According to a further aspect of the present invention there is provided one or more wearable support elements for use with the modular wearable optics device of another aspect of the invention.

According to a further aspect of the present invention there is provided a wearable optical device made from the modular wearable optics device of another aspect of the invention.

According to a further aspect of the present invention there is provided a kit of parts including one or more eyepieces of another aspect of the invention; one or more bridging elements of another aspect of the invention; and one or more wearable support elements of another aspect of the invention.

According to a further aspect of the present invention there is provided an method of selecting a bridging element for the modular wearable optics device of another aspect of the invention, the method comprising: selecting a wearable support element, one or more eyepieces and one bridging element; determining if the configuration of parts has the required optical arrangement for the user; if not changing the one bridging element for another bridging element that is a different shape or size so as to be compatible with the anthropometric characteristic of the user.

DESCRIPTION OF THE INVENTION

In general, the present invention relates to improvement in or relating to wearable optics devices such as HMDs where the problems associated with variable IPD of different users are addressed.

The present invention relates to a novel technique for providing an adjustable, modular HMD or associated kit of parts in which the positions of the eyepieces in an HMD can be varied to suit the IPD and other anthropometric characteristics of each user.

Figure 1:
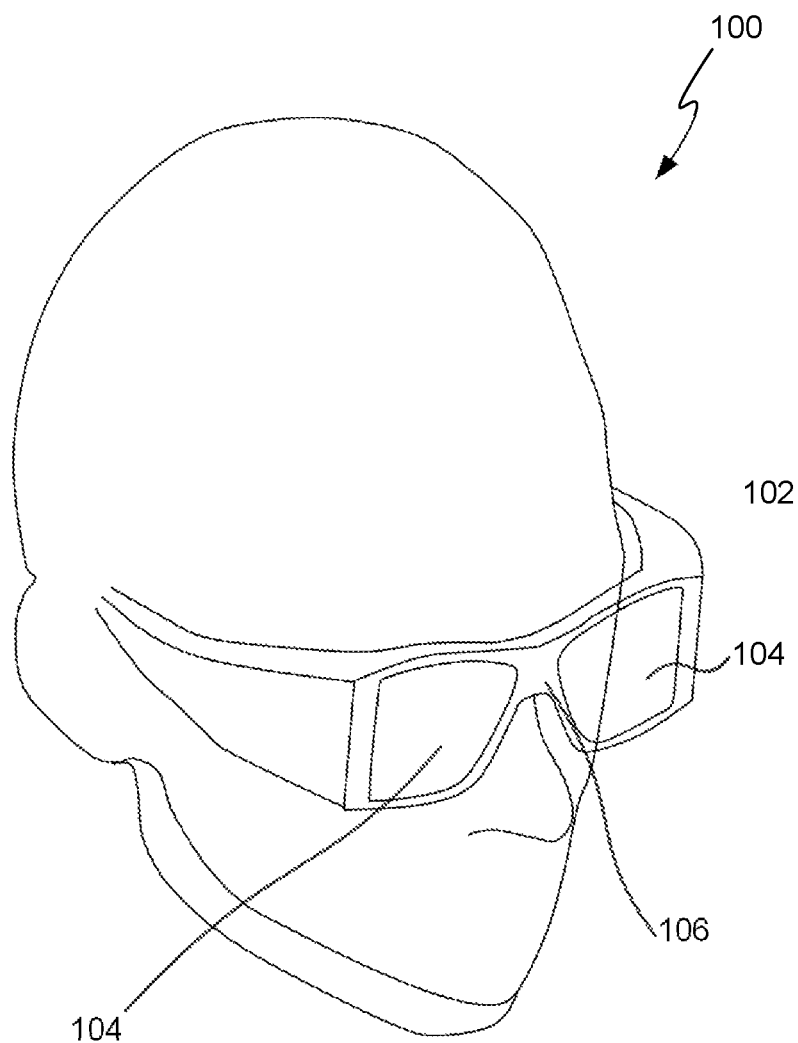
FIG. 1 is a diagram showing a head mounted display, according to an embodiment of the present invention.

FIG. 1 shows a very simple representation of an HMD shown generally at 100. The HMD is wearable by means of an appropriate support 102. The support includes one or more optical elements 104 which can be viewed by one of both eyes of the user. The HMD further includes a control system (not shown).

The HMD can be of any appropriate type including googles, glasses, a helmet or helmet visor, or in the form of a handheld device which can be brought in front of the eyes. Ideally, the device is portable or adapted to be portable by means of the support. Although not shown in detail the support may include a support adapted to support the optical elements in front of the eye. The support may include: frames; side arms and supports for goggles and glasses; a helmet or visor; a headband; a neck or shoulder worn support; a gaming headset; or any other support that could be worn to hold the optical elements in the desired position.

The control system is variable depending on the use of the HMD. The control unit may be in situ or remote from the HMD. The control device may include a communications module for communicating with the optical elements and with other modules either on the HMD or remote therefrom. The communications may be wireless and/or wired. The control module may include different modules for carrying out different functions. These functions are not limited in any way but may include imaging, tracking, scene generation, processing, storage, power supply, audio etc.

Figure 2:
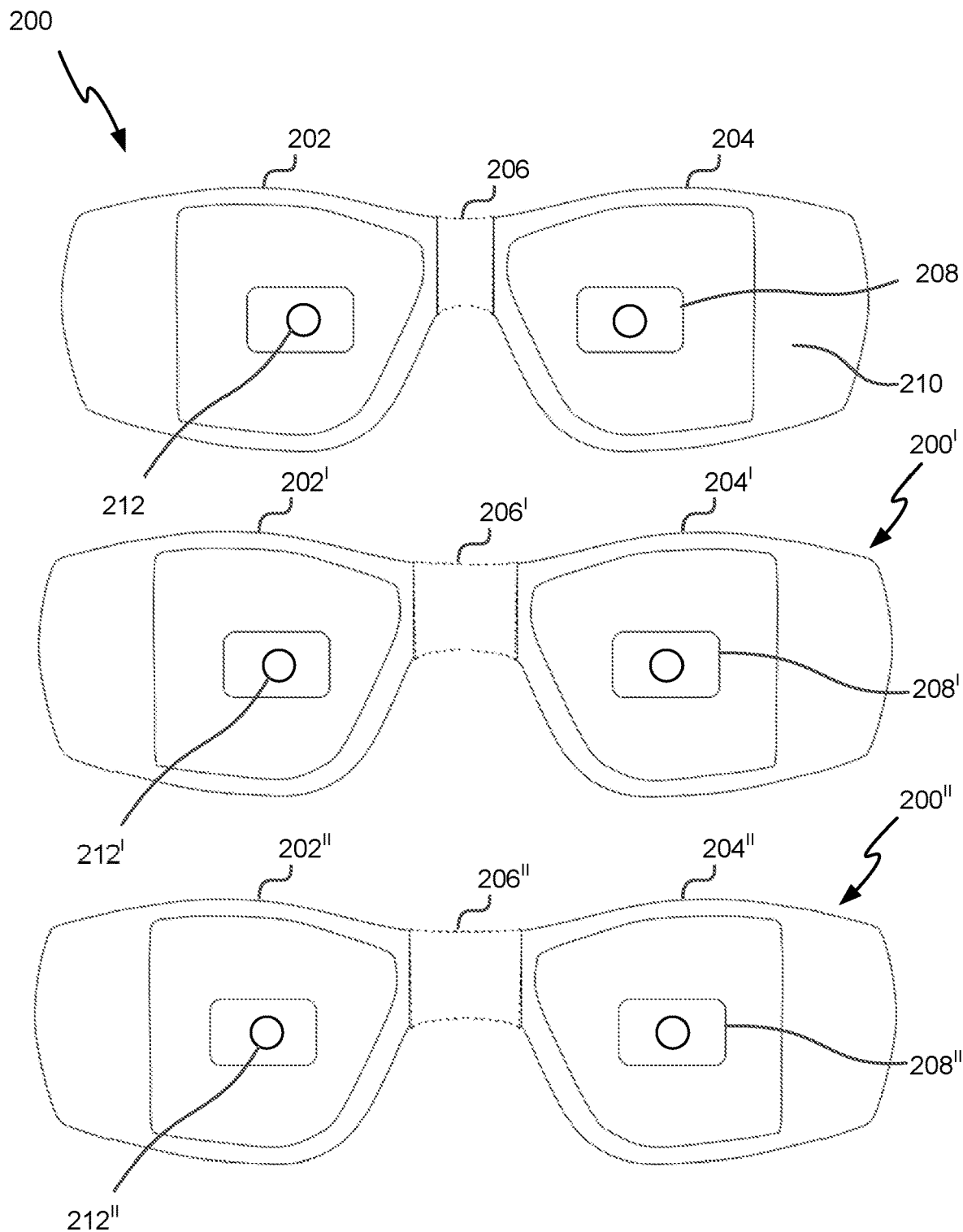
FIG. 2 is a diagram showing representations of two eyepieces in the FIG. 1 device, according to an embodiment of the present invention.

The optical elements 104 may be any appropriate type. Referring to FIG. 2. The optical element 200 includes two eyepieces 202, 204 held together by a bridging element 206. The eyepieces each include a display medium 208 which relays an image to the eye of the user in use. The display medium includes, for example, a waveguide, a lens system, a prism, or other optical components. In FIG. 2 the device is shown as binocular but it is possible that the device could be monocular with one of the display media being replaced with a blank element. The optical elements may be adapted for use in the non-optical domain. It will be appreciated therefore that optical is not limited herein to mean visible optical frequencies and may include non-visible frequencies.

The two eyepieces are separated by a bridging element 206. The bridging element may be a band having a combination of a different curvature and a different length. The bridging element may have a specific shape to position or orient the eyepieces in a predetermined location. More details of the bridging element are described in greater detail below.

Referring again to FIG. 2, the adjustable nature of the HMD will now be described. Each arrangement 200, 200', 200" includes a pair of eyepieces 202, 202', 202" and 204, 204', 204" and a bridging element 206, 206', 206". In order to reduce the active area of each eyepiece the eyepiece may include an active optical area 208 and a blank area 210. The pupil of the eye of a user should be located substantial centrally in the active area for optimal viewing performance. In each arrangement 200, 200' and 200" the position of the pupil of the user is shown for eyepiece 202, 202', 202" as 212, 212' and 212" respectively. The pupil on the other eyepiece is not labelled but is shown.

As can be seen from the different arrangements the separation of the centre of the pupil is different from one arrangement to the next. This is due to the fact that the respective users each have, for example, a different interpupillary distance (IPD). In general, IPD ranges from about 55 mm to about 75 mm. IPD is one anthropometric characteristic that is measured to determine where to locate eyepieces for a particular user. This is not the only anthropometric characteristic or constraint which could be used, others include: eye spacing and height, pupil size, head breadth, nose position, nose size, etc. In addition, the position of the eye of a user may be sunken, bulging or otherwise variable in natures. Occasionally, users even have eyes at different heights relative to one another or be cross-eyed. Further nose shape and width can have a significant influence. Each of the above-mentioned differences affects the required location of the active optical area for each pupil of each user. If the pupil is not correctly oriented relative to the active area portions of the display image may not be visible or visual artefacts may present themselves. To overcome the different positions and orientations of users' pupils the present invention provides a modular assembly including at least one active eyepieces and a plurality of different bridging elements, each of which has a different shape and length to accommodate the differences in the pupil positions and orientations of the user.

The different lengths of bridging elements 206, 206', 206" can be seen in the different arrangement of FIG. 2. The bridging element is attached to the two eyepieces by an appropriate connection on each (not shown). This could include a push connecter, a clip or any other type of mechanical clasp, interface, retainer or connection.

Each bridging element includes an identifier (not shown) which is used to identify one bridging element from the others. The identifier could be a simple label or be an active device which communicates its identity to the system. For example, the identifier may be an RFID identifier or other type of readable electronic label. The identifier may be detectable by the eyepieces and/or the HMD to enable identification of the bridging element for a number of different reasons as will be described below. The main purpose of the identifier is to enable the system to determine the combination of eyepieces and bridging element used for a particular user. This is important as the end orientation and position of the eyepieces relative to one another is required to ensure that any image displayed to the HMD is delivered correctly.

A number of examples of possible bridging elements can be imagined and are in no way limited. The bridging elements may have different length and curvatures to accommodate different nose shapes and eye positions and orientations on the face. The bridging elements are made of material which can retain its shape even when connected and unconnected multiple times. In addition, the bridging element can be reseated as often as necessary. Typical materials may include consumer grade metals, plastics, polymers or rubbers as known in the industry.

In one example, the bridging elements may be connected to the eyepieces by a magnetic connection. This example may only be applicable to uses where magnetic forces will not interfere with the optical and electronic components of the HMD. Again as discussed above the relevant combinations of eyepieces and bridging element are identified by the identifiers to enable the orientation and position of the respective eyepieces.

Figure 3:
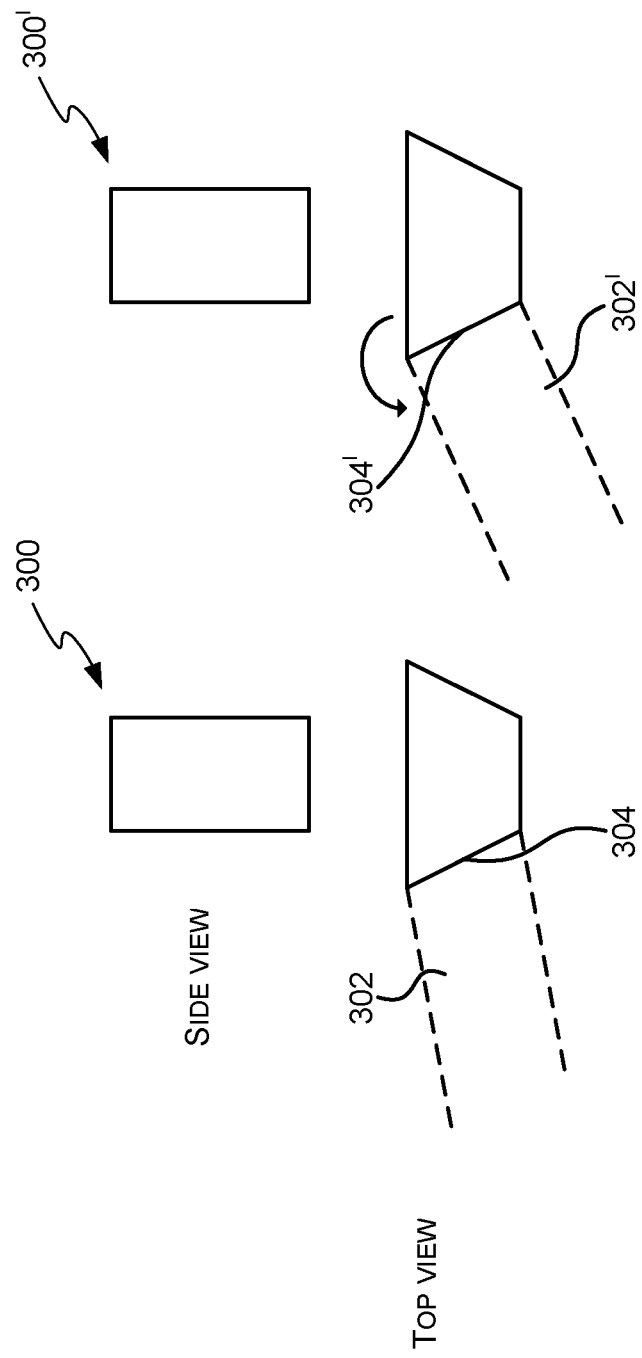
FIG. 3 is diagram showing a second type of bridging element, according to an embodiment of the present invention.

Referring to FIG. 3, the position of the bridging elements 300, 300' may be moveable relative to the eyepieces 302, 302' to different angular positions. As shown in the LHS of the drawing the angle in one instance may be less slanted than that of another orientation as shown in the RHS of the drawing. This could be achieved by having a pivot about which the bridging element can rotate or, as shown, could be based on a particular shape of the bridging element. For example, the bridging element 300 on the LHS is approaching a near rectangle wedge shape in the view from above and the eyepieces are aligned with angled side 304. This produces a certain angular displacement in the orientation of the eyepiece relative to the bridging element. On the other hand, the bridging element 300' on the RHS is shaped in the form of a rhombus in the view from above and the eyepieces are aligned with angled side 304', which produces a larger bend in the orientation of the eyepiece relative to the bridging element. Different angular alignments can be achieved by using different shaped bridging elements. Each different shape or slant of the bridging element may include an identifier as discussed above which gives an indication of the angular orientation of the bridging element relative to the eyepiece. This could be the same or a different RFID or other type of electronic or readable label.

One effect of using the angled bridging elements is that the HMD can give rise to a wider perceived field of view (FOV) than if the eyepieces were not angularly displaced. As each eyepiece is orientated off the nominal axial display path, the perceived display FOV will now comprise of a central stereoscopic region where the FOV from each eyepiece overlaps and a FOV region outside of this central region where the FOV from each eyepiece does not overlap. This will typically result in a wider binocular FOV comprising the central FOV region and FOV at the edges of the central region; this will be perceived as a wider FOV by the user.

The bridging element may be adjustable. Different ways of implementing a variable length bridging element can be envisaged.

The present invention is aiming to provide a flexible and adjustable HMD which can be adapted for use with different users by adjusting the position and orientation of the eyepieces through a plurality of variable bridging elements. The nose pieces may be have one or more differences in terms of shape, size (including variable length), angular orientation and relative position of the respective eyepieces. The present invention achieves this through a modular system. The modular system includes one or more housing or support modules, a control module (which may be remote), one or more eyepieces, and plurality of bridging elements. A HMD may be constructed from any combination of these elements and any number of modules can be provided as a single package to a user. The user then selects the support, eyepieces and bridging element that best suits their needs.

For example, one user may chose two active eyepieces and a frame that fits their heads and one of the bridging elements. The user then combines the combinations of parts into a HMD that is adapted to their vision. Another user may select one active eyepiece and one "blank" eyepiece and connect the two to side arms for glasses and connect the eyepieces with one of the bridging elements. The combinations are endless and each user can easily adapt the HMD to their required vision and operational requirements.

Figure 4:
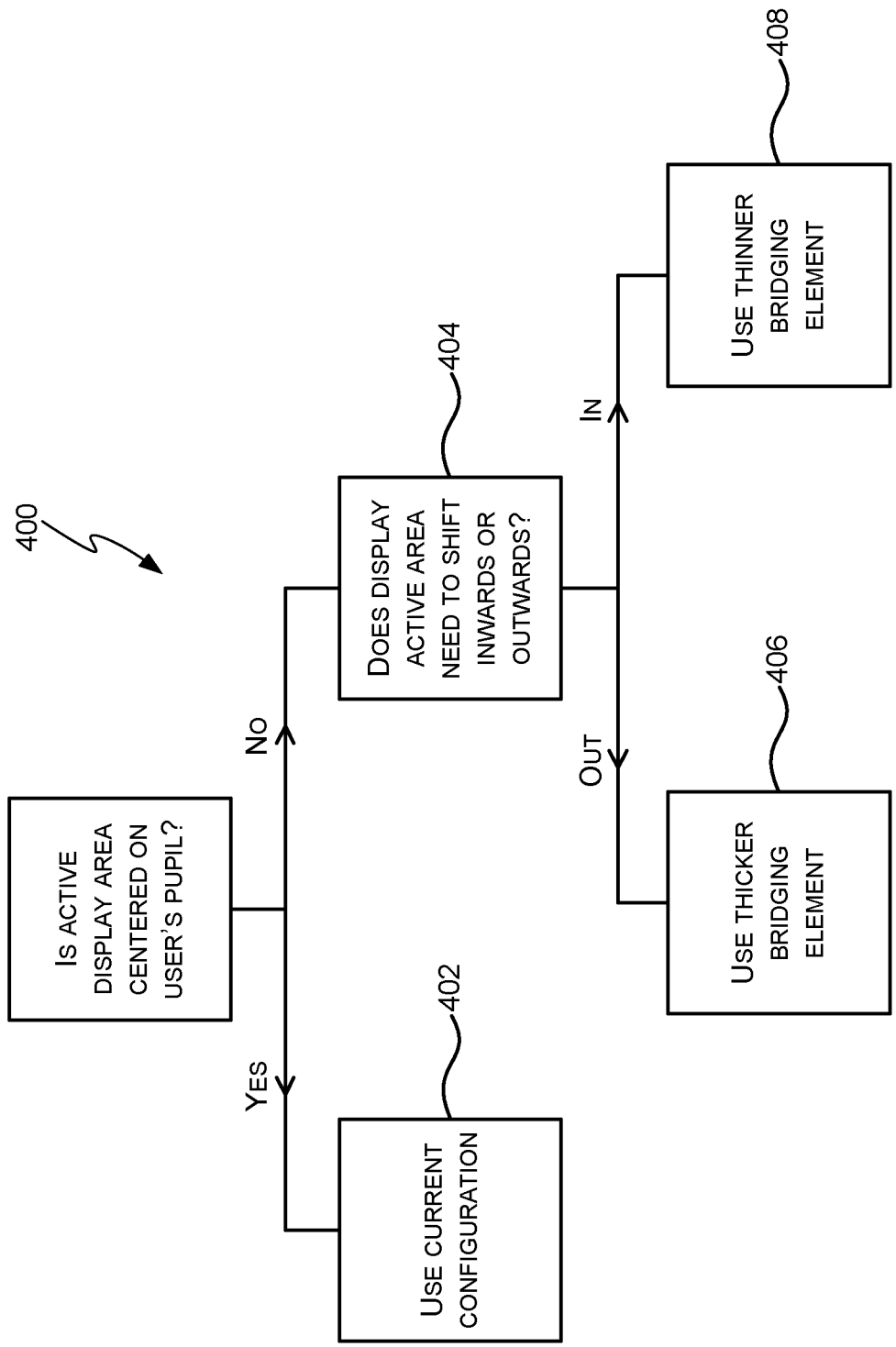
FIG. 4 is diagram showing a flow chart for selecting the correct bridging element, according to an embodiment of the present invention.

FIG. 4 is a simple flow chart showing how a user might decide which bridging element to use. The user puts together a combination of support, eyepieces and bridging element 400. If their visionary requirements are correct (yes), this configuration is used 402. If their visionary requirements are incorrect (no) the process advances to step 404. Here for example, the IPD of the user is assessed to determine in the IPD of the configurations is appropriate for the user. If the configuration is incorrect the nature of the problem is ascertained. A determination is made as to whether the active display area needs to shift inwards or outwards 404. If outwards, a longer or thicker bridging element is selected 406 and if inwards, a shorter or thinner bridging element is selected 408.

The present invention provides a number of clear advantages, example of which are now discussed.

An HMD is a relatively expensive piece of equipment and as such it is undesirable to have more than is needed. By providing a modular system in accordance with present invention a single set of eyepieces can be provides with multiple bridging elements making the HMD adaptable to all users without having to have a device for each user. In addition, as the configuration is adapted to the IPD of each user by varying the relative position of the eyepieces it is possible to have a smaller active area in each eyepiece as this does not have to be expanded to accommodate users having different IPDs, this has performance benefits. Instead, this is accommodated by a relatively inexpensive set of bridging elements. In some situations it is useful to have only one active eyepiece and in others two are preferable. By having a two or more eyepieces, one of which may be inactive, different configurations may be accommodated. In addition, by having different supports or houses individual preference and other issues such as safety and robustness of the HMD are also provided.

As will be appreciated the present invention relates to an adjustable wearable optic device such as an HMD. It could equally apply to different devices, including but not limited to HWD and other optical devices.

Although the present invention has been described in connection with some embodiments, it is not intended to be limited to the specific form set forth herein. Rather, the scope of the present invention is limited only by the accompanying claims. Additionally, although a feature may appear to be described in connection with particular embodiments, one skilled in the art would recognize that various features of the described embodiments may be combined in accordance with the invention. In the claims, the term 'comprising' does not exclude the presence of other elements or steps.

Furthermore, the order of features in the claims does not imply any specific order in which the features must be performed and in particular the order of individual steps in a method claim does not imply that the steps must be performed in this order. Rather, the steps may be performed in any suitable order. In addition, singular references do not exclude a plurality. Thus, references to 'a', 'an', 'first', 'second', etc. do not preclude a plurality. In the claims, the term 'comprising' or "including" does not exclude the presence of other elements.

The invention claimed is:

1. A modular wearable optics device including:
   at least one wearable support element, to be worn by a user;
   one or more active optical elements adapted in use to display an image to a user; and
   a removable bridging element, selected from a plurality of bridging elements, to position or orientate the one or more active optical elements in a predetermined location based on one or more anthropometric characteristics of the user, wherein the plurality of bridging elements have different shapes and sizes each adapted to locate the one or more active optical elements in a different position or orientation;
   wherein the selected bridging element includes an identifier which enables identification of the shape and size of the bridging element by a control system of the one or more active optical elements to thereby adjust one or more convergence parameters of the one or more active optical elements based on the identified shape and size of the selected bridging element.

2. The modular wearable optics device of claim 1, further comprising the control system configured to adjust the one or more convergence parameters of the one or more active optical elements.

3. The modular wearable optics device of claim 1, wherein the identifier is at least one of an active device, an electronic label, and/or a radio frequency identifier (RFID).

4. The modular wearable optics device of claim 1, wherein the one or more active optical elements are adapted to be angularly displaceable to create a wider field of view.

5. The modular wearable optics device of claim 1, wherein the one or more anthropometric characteristics are based on the interpupillary distance of the user.

6. The modular wearable optics device of claim 5, wherein the selected bridging element is selected based on the interpupillary distance of the user.

7. The modular wearable optics device of claim 1, wherein each of the one or more active optical elements includes an active optical area that is surrounded by an inactive area.

8. The modular wearable optics device of claim 1, wherein the wearable support element comprises one or more of: a frame; side arms and supports for goggles or glasses; a helmet; a visor; a headband; a neck-worn support; a shoulder-worn support; and/or a headset.

9. The modular wearable optics device of claim 1, wherein one or more bridging elements of the plurality of bridging elements is a band having a combination of a different curvature and a different length.

10. The modular wearable optics device of claim 1, wherein a first bridging element of the plurality of bridging elements is a first shaped element adapted to support the one or more active optical elements in a first predetermined position or orientation, and a second bridging element of the plurality of bridging elements is a second shaped element adapted to support the one or more active optical elements in a second predetermined position or orientation that is different from the first predetermined position or orientation.

11. A head mounted display comprising the modular wearable optics device of claim 1.

12. The modular wearable optics device of claim 1, wherein the at least one wearable support element comprise glasses or goggles configured to support an eyepiece, and the eyepiece includes one of the one or more active optical elements.

13. The modular wearable optics device of claim 12, wherein the eyepiece is a first eyepiece, the modular wearable optics device further including a second eyepiece, wherein the glasses or goggles are configured to support the second eyepiece, and the first and second eyepieces are directly attachable to the selected bridging element.

14. The modular wearable optics device of claim 12, wherein the identifier includes an active device and/or an electronic label, the active device and/or electronic label associated with both a particular user and a preestablished orientation and position of the eyepiece.

15. A kit of parts for a wearable optical device, the kit including:
an eyepiece including an active optical area, the active optical area including a display medium configured to relay an image to an eye of a user;
a plurality of bridging elements, each bridging element having a different shape and size adapted to locate the active optical area in a different position and/or orientation; and
a wearable support element configured to support the eyepiece;
wherein the eyepiece is adapted to be angularly displaceable to create a wider field of view.

16. The kit of parts of claim 15, wherein each bridging element of the plurality is directly attachable to the eyepiece.

17. The kit of parts of claim 15, wherein each bridging element includes an identifier which enables identification of the shape and size of the bridging element by a control system to thereby adjust one or more convergence parameters of the active optical area based on the identified shape and size of the selected bridging element.

18. A method for providing a modular wearable optics device to meet a required optical arrangement for a user, the method comprising:
selecting a wearable support element, one or more eyepieces, and one bridging element from a plurality of bridging elements, wherein the plurality of bridging elements have different shapes and sizes each adapted to locate the one or more eyepieces in a different position or orientation, and wherein each bridging element includes an identifier which enables identification of the shape and size of the bridging element by a control system of the one or more active optical elements;
determining if the configuration of selected parts has the required optical arrangement for the user;
in response to the configuration of selected parts not meeting the required optical arrangement for the user, changing the one bridging element for another bridging element included in the plurality and that is a different shape and/or size so as to be compatible with an anthropometric characteristic of the user; and
adjusting, with the control system, one or more convergence parameters of the one or more eyepieces based on the identified shape and size of the other bridging element.

* * * * *